(12) United States Patent
Gobaa et al.

(10) Patent No.: US 10,379,107 B2
(45) Date of Patent: Aug. 13, 2019

(54) METHOD FOR PREPARING TOPOGRAPHICALLY STRUCTURED MICROARRAYS

(75) Inventors: Samy Gobaa, Prilly (CH); Matthias Lutolf, Tolochenaz (CH)

(73) Assignee: Ecole Polytechnique Federale de Lausanna (EPFL), Lausanne (CH)

(*) Notice: Subject to any disclaimer, the term of this patent is extended or adjusted under 35 U.S.C. 154(b) by 701 days.

(21) Appl. No.: 14/344,477

(22) PCT Filed: Sep. 12, 2012

(86) PCT No.: PCT/EP2012/067856
§ 371 (c)(1),
(2), (4) Date: Apr. 4, 2014

(87) PCT Pub. No.: WO2013/037836
PCT Pub. Date: Mar. 21, 2013

(65) Prior Publication Data
US 2016/0202244 A1 Jul. 14, 2016

(30) Foreign Application Priority Data
Sep. 12, 2011 (CH) ................................ 1507/11

(51) Int. Cl.
| | |
|---|---|
| *G01N 33/50* | (2006.01) |
| *B01J 19/00* | (2006.01) |
| *C12N 5/00* | (2006.01) |
| *G03F 7/20* | (2006.01) |
| *G03F 7/32* | (2006.01) |
| *G03F 7/36* | (2006.01) |
| *C12Q 1/02* | (2006.01) |

(52) U.S. Cl.
CPC ...... *G01N 33/5041* (2013.01); *B01J 19/0046* (2013.01); *C12N 5/0068* (2013.01); *C12Q 1/02* (2013.01); *G01N 33/5026* (2013.01); *G01N 33/5032* (2013.01); *G03F 7/20* (2013.01); *G03F 7/32* (2013.01); *G03F 7/36* (2013.01); *B01J 2219/00385* (2013.01); *B01J 2219/00509* (2013.01); *B01J 2219/00596* (2013.01); *B01J 2219/00722* (2013.01); *B01J 2219/00725* (2013.01); *B01J 2219/00731* (2013.01); *C12N 2535/10* (2013.01)

(58) Field of Classification Search
None
See application file for complete search history.

(56) References Cited

U.S. PATENT DOCUMENTS

| | | | |
|---|---|---|---|
| 6,174,683 B1 | 1/2001 | Hahn et al. | |
| 6,372,813 B1 | 4/2002 | Johnson et al. | |
| 7,588,906 B2 | 9/2009 | Brueggemeier et al. | |
| 7,595,157 B2 | 9/2009 | Tsinberg | |
| 2003/0044389 A1 | 3/2003 | Brown et al. | |
| 2005/0156499 A1* | 7/2005 | Dinu ...................... | G02F 1/065 313/310 |
| 2006/0160066 A1 | 7/2006 | Bhatia et al. | |
| 2010/0055733 A1 | 3/2010 | Lutolf et al. | |

OTHER PUBLICATIONS

Gobaa et al., "Artificial niche microarrays for probing single stem cell fate in high throughput", Nature Methods, XP-055011759, Nov. 2011, vol. 8, No. 11, pp. 949-957, Nature America, Inc., New York, NY.
Burdick et al., "High-throughput stem-cell niches", Nature Methods, XP-002663337, Nov. 2011, vol. 8, No. 11, pp. 915-916, Nature America, Inc., New York, NY.
Charnley et al., "Integration column: microwell arrays for mammalian cell culture", Integrative Biology, XP-002663338, Oct. 1, 2009, pp. 625-634, The Royal Society of Chemistry, London, UK.
Cordey et al., "Enhancing the Reliability and Throughout of Neurosphere Culture on Hydrogel Microwell Arrays", Stem Cells, XP-002663339, Jul. 26, 2008, pp. 2586-2594, AlphaMed Press, Durham, NC.
Brammer et al., "Hydrophobic nanopillars initiate mesenchymal stem cell aggregation and osteo-differentiation", Acta Biomaterialia, XP-27577079, Sep. 7, 2010, pp. 683-690, Elsevier Ltd., Amsterdam, NL.

(Continued)

*Primary Examiner* — Christopher M Gross
(74) *Attorney, Agent, or Firm* — Davis & Bujold PLLC; Michael J. Bujold

(57) ABSTRACT

A method for preparing a topographically structured hydrogel microarray is described comprising the steps of a) providing one or more types of biomolecule(s) on top of micropillars of an array of micropillars, preferably by means of robotical spotting, b) providing a partially crosslinked hydrogel on a substrate, preferably attached to a substantially rigid and/or planar substrate, c) simultaneously soft-embossing a hydrogel microwell array and transferring the biomolecule(s) from the micropillars to the microwells by pressing the micropillars of the array of step a) onto the partially crosslinked layer of hydrogel of step b) until substantial completion of crosslinking and d) demolding the array of micropillars of step a) from the hydrogel microwell array of step c). The method according to the invention has the advantages of resulting in higher biochemical patterning precision, allowing for modulation of biochemical parameters by interfacing microarray manufacture with robotic technology and rendering the microarrays obtained compatible with existing read-out systems such as microscopes. Further, the elasticity of the hydrogel can be varied by tuning its shear modulus.

6 Claims, 11 Drawing Sheets

Specification includes a Sequence Listing.

(56) References Cited

OTHER PUBLICATIONS

Lutolf et al., "Perturbation of single hematopoietic stem cell fates in artificial niches", Integrative Biology, XP-002608475, Nov. 1, 2008, pp. 59-69, The Royal Society of Chemistry, London, UK.
Kobel et al., "Micropatterning of Hydrogels by Soft Embossing", XP-55011765, Langmuir Article, Jan. 2009, 25 (15), pp. 8774-8779, American Chemical Society, Washington, DC.

* cited by examiner

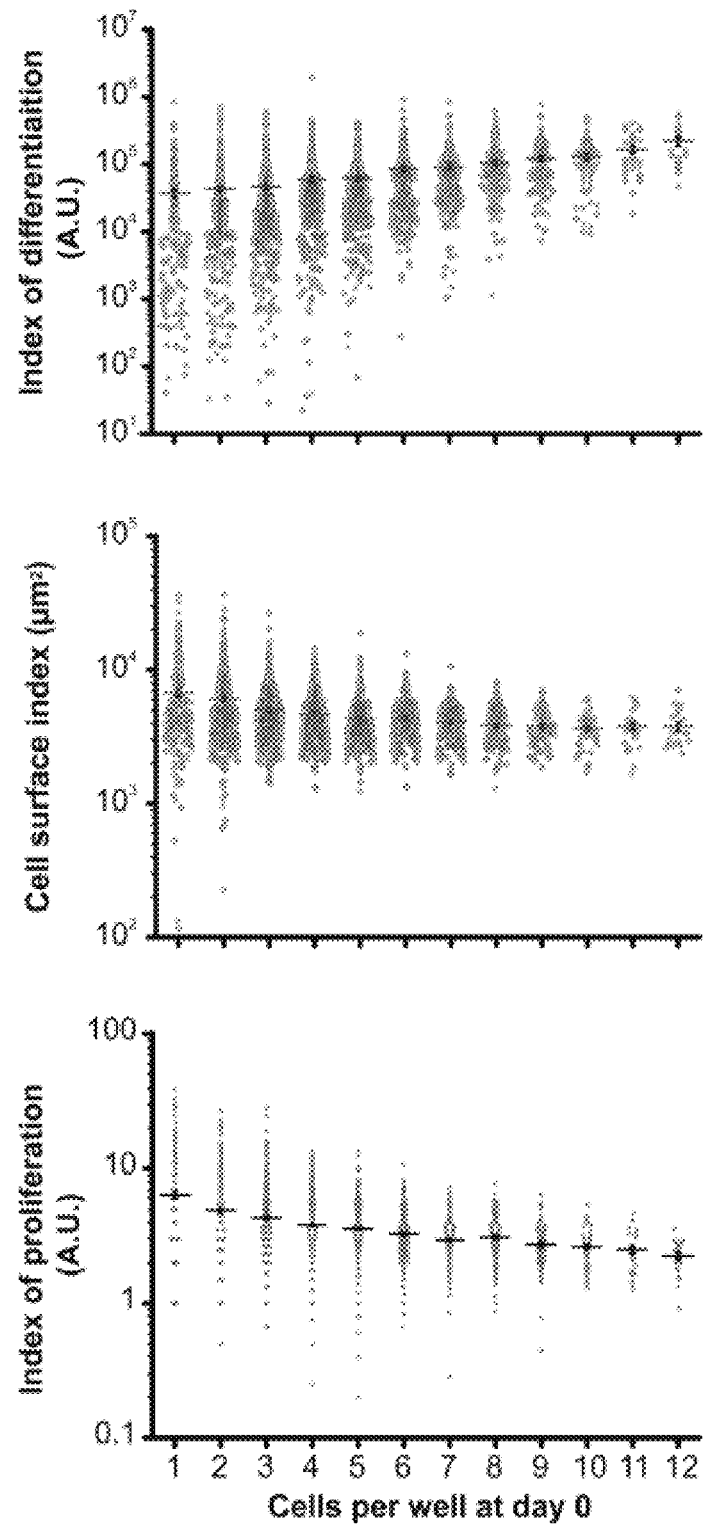
Fig. 2c-e:

Fig. 3d-g:
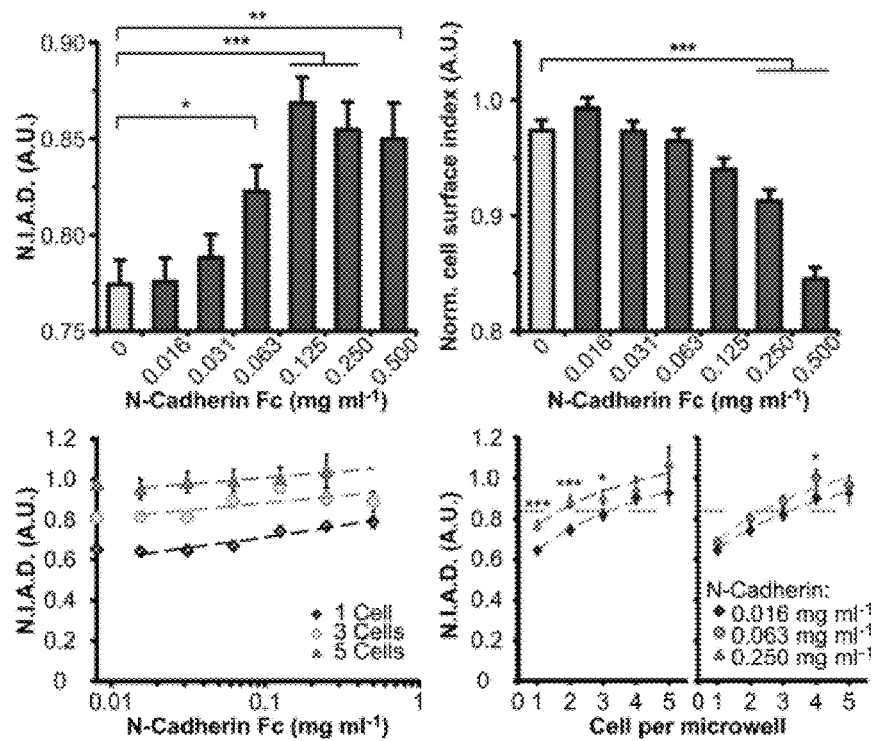
Fig. 3h-i:
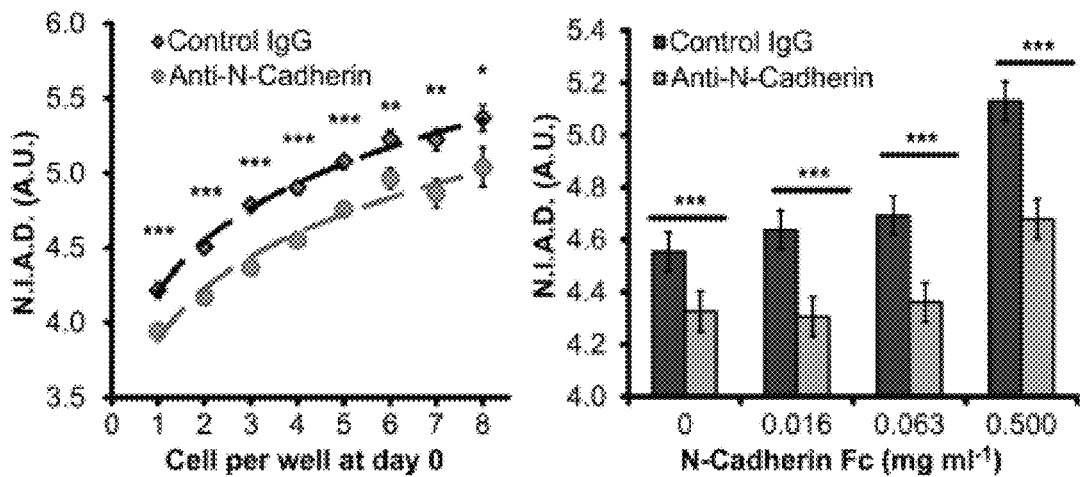

Fig. 4d-e:
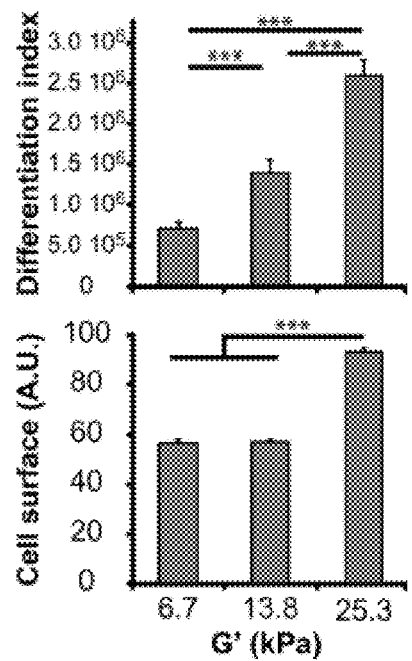
Fig. 4f
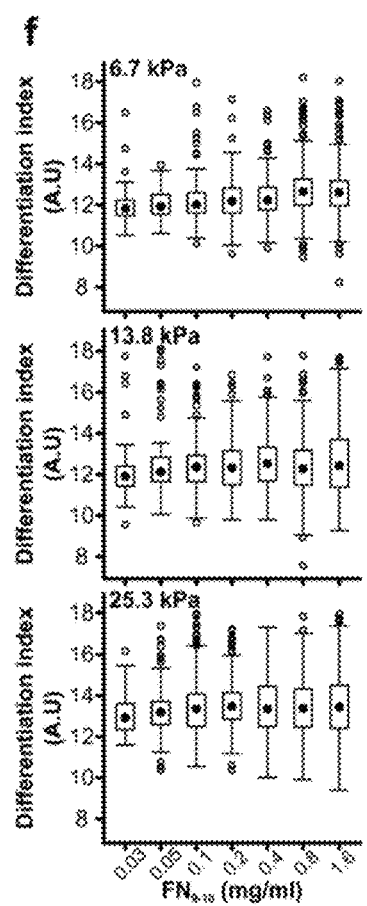

SEQUENCE LISTING

<160> NUMBER OF SEQ ID NOS: 6

<210> SEQ ID NO 1
<211> LENGTH: 20
<212> TYPE: DNA

```
<213> ORGANISM: Homo sapiens

<400> SEQUENCE: 1
ggcagaagag agactgggtc                                                     20

<210> SEQ ID NO 2
<211> LENGTH: 20
<212> TYPE: DNA
<213> ORGANISM: Homo sapiens

<400> SEQUENCE: 2
gaggctggtc agctcctggc                                                     20

<210> SEQ ID NO 3
<211> LENGTH: 21
<212> TYPE: DNA
<213> ORGANISM: Homo sapiens

<400> SEQUENCE: 3
gagatttctc tgtatggcac c                                                   21

<210> SEQ ID NO 4
<211> LENGTH: 21
<212> TYPE: DNA
<213> ORGANISM: Homo sapiens

<400> SEQUENCE: 4
ctgcaaatga gacactttct c                                                   21

<210> SEQ ID NO 5
<211> LENGTH: 19
<212> TYPE: DNA
<213> ORGANISM: Homo sapiens

<400> SEQUENCE: 5
gaaggtgaag gtcggagtc                                                      19

<210> SEQ ID NO 6
<211> LENGTH: 20
<212> TYPE: DNA
<213> ORGANISM: Homo sapiens

<400> SEQUENCE: 6
gaagatggtg atgggatttc                                                     20
```

METHOD FOR PREPARING TOPOGRAPHICALLY STRUCTURED MICROARRAYS

BACKGROUND OF THE INVENTION

The present invention relates to a method for preparing a microarray comprising a hydrogel layer topographically structured with microwells for screening and cell culture experiments as well as said microarray itself. The invention can be employed in high throughput cell screening for pharmaceutical and diagnostic applications, basic biological studies, genetic assays, in systematic cellular knock-down, regenerative medicine and in tissue engineering. Specifically, the invention is useful for studying in vitro mammalian somatic stem cells and elucidating the role the microenvironment (niche) of these cell plays in stem cell fate, i.e. in differentiation, self-renewal and proliferation.

Microarrays for biomolecular and/or cellular probes as such are well known and widespread.

US 2006/0160066 A1 relates to a microarray platform for the culture of cells comprising a plurality of microspot islands on or microwells in a hydrogel substrate, wherein said microspot islands or microwells comprise an insoluble factor or an insoluble and soluble factor, wherein the insoluble factor promotes cellular adhesion.

US 2003/0044389 A1 describes a method of profiling cells with respect to their ability to respond to external biochemical stimuli in the microenvironment, which involves arraying cells on a planar surface through binding to immobilized probes such as signaling cues and specific binding partners for cell surface molecules.

U.S. Pat. No. 7,595,157 B2 discloses a microarray for assaying a target material in a biological sample comprising a solid, flat substrate functionalized with organic molecules, a polymerized hydrogel layer including anchoring moieties and a plurality of different probes linked to the anchoring moieties in the polymerized hydrogel layer to create microspots.

U.S. Pat. No. 7,588,906 B2 relates to a method of attachment of biomolecules such as peptides and proteins by immobilization on modified surfaces through a polyacrylamide-based polymerization reaction.

U.S. Pat. No. 6,372,813 B1 relates to a method for preparing a crosslinked polyacrylamide hydrogel array comprising one or more attached biomolecules, whereby attachment occurs via 2+2 photocycloaddition between one or more reactive sites of the biomolecule and on the polyacrylamide reactive prepolymer.

U.S. Pat. No. 6,174,683 B1 describes a method for preparing a biochip comprising a solid substrate to which is bound covalently a polyurethane-based hydrogel derivatized with covalently bound biomolecules.

Thus, from the prior art the use of hydrogels for microarrays, to which biomolecules are attached, is known. These arrays exist in the form of microspots on planar surfaces as well as microwells etched into the hydrogel and can be used for studying the biochemical microenvironment of adherent cells.

There is, however, no microarray which allows for analysis of both biochemical and biophysical niche effectors separately or simultaneously for adherent as well as non-adherent cells. Further, due to the spotting techniques used to distribute biomolecules in microwells of known microrrays, there is little spotting precision and limited possibility of modulating biochemical parameters.

SUMMARY OF THE INVENTION

The objective of the present invention is to provide a microarray, which is able to overcome the above limitations and drawbacks of the prior art.

An advantage of the invention is that it allows for simultaneous investigation of both biochemical niche effectors (signalling cues), such as proteins or peptides controlling cell-cell interactions, ECM molecules and soluble factors, and biophysical cues such as niche (microenvironment) elasticity or geometry on cell response by varying and tuning the shear modulus of the hydrogel employed. Thus, novel factors and microenvironments controlling a particular (stem) cell function (self-renewal, differentiation, proliferation) can be identified. Where different biochemical or biochemical and biophysical signalling cues are present, these can also be investigated separately by decoupling them from each other.

Both cell culture efficiency and screening power are enhanced.

A further advantage of the invention is that it allows adherent as well as non-adherent cells to be studied at the single cell level. No attachment of cells to the micoarray is necessary as cells are trapped by gravitational sedimentation within the wells while the distribution of captured cells per well depends on the overall number of cells seeded.

Another objective of the present invention is to provide a method for preparing a microarray.

Said method has the advantage of resulting in higher biochemical patterning precision, e.g. well-controlled biomolecule concentrations within wells, and allowing for modulation of biochemical parameters by interfacing microarray manufacture with robotic technology. Further, it renders the microarrays obtained compatible with existing read-out systems such as microscopes.

Each microwell may contain a different type, mixture or amount of biomolecule of interest. Biomolecule patterning is free of any neighbouring or repetition constraints, allowing the generation of overlapping gradients and random patterns equally well.

Further, it has been found that the method for preparing a microarray according to the invention allows for the preparation of large-scale microarrays as well as microarrays having smaller formats particularly useful in screening or cell culture experiments using combinations of both tethered and soluble niche factors as hydrogel swelling of the selected gel formulations is limited. Thus, microwell dimensions are highly conserved and no delamination of the hydrogel layer from the rigid substrate is observed, even after several weeks in culture.

Further objectives of the present invention are to provide an array of micropillars used as a stamp in the preparation of a microarray according to the invention, a method of preparing said array of micropillars and a kit of parts comprising an array of micropillars, a rigid substrate and reactants suitable for the formation of a hydrogel having a shear modulus of between 1 and 100 kPa.

DETAILED DESCRIPTION OF THE INVENTION

Figure 1A:
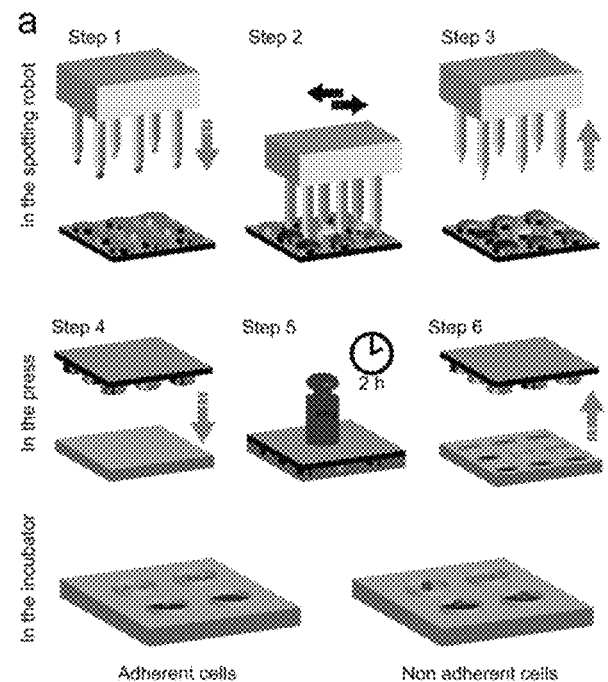
FIGS. 1 *a* and *b* depict the preparation of an artificial niche microarray and examples of protein patterns obtained on microwell substrates, respectively. Steps (1) to (6) show the individual preparation steps: (1) A DNA spotter equipped with solid pins (diameter: 300 mm) is used to spot desired protein solutions on micropillars of a microfabricated silicon stamp. The micropillars have a diameter of 450 µm and a height of 80 to 100 µm. (2) The topology of the silicon stamp and the printing scheme of the robot are matched to ensure the localization of the spotting onto the micropillars. (3) Multiple cycles of printing are carried out to cover all of the 2016 micropillars of one stamp. Up to 4 stamps can be printed in parallel. (4) The printed stamps are pressed against a thin, partially crosslinked layer of PEG hydrogel. (5) Concomitant microwell soft-embossing and localized protein tethering for 2 hours until completion of crosslinking. (6) Stamp is demolded from patterned hydrogel layer. The obtained artificial niche microarray can be seeded with either adherent or non-adherent stem cells.
FIG. 1b shows a representative example of two full arrays (stitched together in mosaic fashion from individual images) spotted with two fluorescently labelled BSA model proteins. Six concentrations of FITC-BSA and six concentrations of Rhodamin-BSA are printed either in 12×12 random motifs (left) or as overlapping gradients (right), all in the context of a topographically patterned gel substrate (bottom image on the right: 3D-reconstruction of confocal stacks).
Figure 1B:
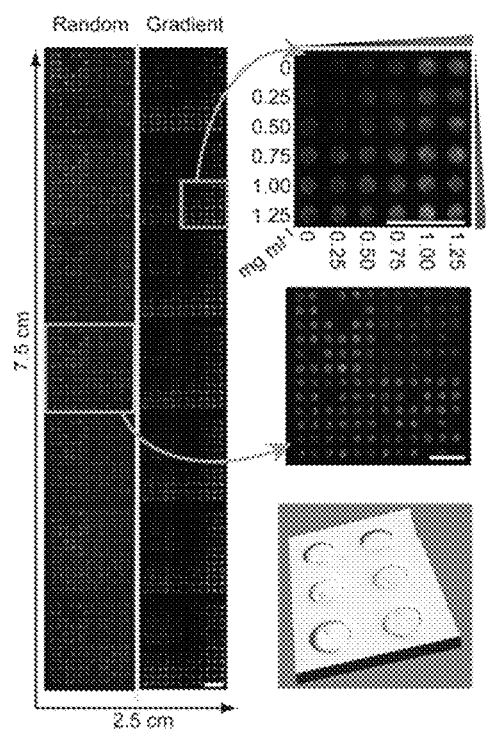

In a first aspect, the present invention relates to a microarray to be used in screening or cell culture experiments and comprising a substrate, which is preferably substantially rigid and/or planar rigid, and a hydrogel layer on said substrate, wherein the hydrogel is topographically structured with microwells, characterized in that the hydrogel layer has a shear modulus (stiffness) between 1 and 100 kPa, which corresponds to am E-modulus between 3 to 300 kPa assuming a Poisson ratio of 0.5. Shear moduli G' of hydrogels were obtained by rheometry under small strain oscillatory shear at room temperature and at a constant strain of 0.05. Hydrogels of 1 to 1.4 mm thickness were sandwiched between the two plates of a rheometer with compression up to 70% of their original thickness to avoid slipping.

Said screening experiments encompass high throughput cellular screening, cellular screening for pharmaceutical, diagnostic or clinical applications, basic biological studies, genetic assays, gene expression studies, systematic cellular knock-down, regenerative medicine and tissue engineering.

The hydrogel used is a soft, biomimetic, i.e. physiologically relevant, gel. The hydrophilic polymer to form a hydrogel is preferably selected from the group consisting of poly(ethylene glycol), poly aliphatic polyurethanes, polyether polyurethanes, polyester polyurethanes, polyethylene copolymers, polyamides, polyvinyl alcohols, poly (ethylene oxide), polypropylene oxide, polyethylene glycol, polypropylene glycol, polytetramethylene oxide, polyvinyl pyrrolidone, polyacrylamide, poly(hydroxy ethyl acrylate), poly(hydroxyethyl methacrylate). The polymer chains are crosslinked from at least two precursor components using a chemical reaction, wherein the first precursor component comprises n nucleophilic groups and the second precursor component comprises m electrophilic groups, wherein n and m are at least two and the sum n+m is at least five.

Preferably, a hydrogel composed of a hydrophilic polymer such as poly(ethylene glycol)(PEG) with an excess of free functional groups, preferably nucleophilic groups, more preferably chosen from the group comprising amines and thiols, and in addition or alternatively, electrophilic groups, preferably chosen from the group comprising acrylates, methacrylates, acylamides, methacrylamide, acylonitriles, quinines, vinylsulfones, maleimides and their derivatives, is used. PEG-based hydrogels are relatively inert to protein adsorption, thus resisting cell adhesion even without dedicated passivation strategies. At the same time, PEG-based hydrogels are readily functionalized with one or more types of biomolecules of interest such as proteins, oligopeptides and oligonucleotides and may be modified with respect to their shear moduli. Due to their soft and hydrophilic properties, PEG-hydrogels facilitate highly precise and homogeneous patterning of their surface layers.

Preferably, a micro- to millimolar excess of free functional groups such as thiols within the hydrogel is obtained.

Preferably, the hydrogel of the microarray according to the invention is prepared by crosslinking hydrophilic polymer macromers at various concentrations in order to adjust stiffness and in such a way as to obtain an excess of free functional groups.

Preferably, the cross-linking is conducted between a multi-arm-PEG macromer, preferably a four-arm PEG macromer having a molecular weight of 10 kDa and end-functionalized with nucleophilic, preferably thiol groups and a multi-arm-PEG macromer, preferably an eight-arm PEG macromer having a molecular weight of 10 kDa and end-functionalized with electrophilic, preferably vinylsulfone groups at appropriate concentrations and conditions such as to allow for the crosslinked hydrogel layer to exhibit a shear modulus between 1 and 100 kPa.

The free functional groups, preferably thiols, which are present in excess within the formed hydrogel, provide chemical handles for the tethering of biomolecules to the surface of the hydrogel, i.e. the functionalization of the hydrogel with biomolecules, within the microwells.

Preferably, the hydrogel of the microarray according to the invention is prepared from specific macromers to not swell or swell minimally (<10% in volume) such as to not alter the dimensions of the embossed microwells. Non-swelling or minimally swelling hydrogels are obtained by choosing highly functional macromers with specific molecular weights.

Biomolecules may e.g. be small molecules such as natural products or macromolecules selected from the group of proteins, oligopeptides or oligonucleotides, polynucleotides, oligo- or polysaccharides. These biomolecules employed are either known or expected to influence cell fate and fall into the categories of ECM-derived or ECM-mimetic proteins such as fibronectin, laminins, collagens and their functional oligopeptidic analogues (e.g. RGD mimicking the integrin ligand fibronectin), chimeric/tagged proteins, functionalized oligopeptides and functionalized oligonucleotides. The tagged proteins include those having Fc-tags (Fc-tagged N-Cadherin, biotin-tags or His-tags such as to enable binding to ProteinA (or ProteinG), Streptavidin (or NeutrAvidin) or NTA. The functionalized oligopeptides and oligonucleotides include those having nucleophilic or electrophilic functional groups such as thiols or vinylsulfone or maleimide that can react with the functional groups on the polymers that make up the hydrogel network.

The biomolecule categories require different tethering strategies to the PEG-based hydrogel layer. Larger ECM-derived or ECM-mimetic proteins and peptides are attached to the hydrogel by non-specific tethering using linear, heterodifunctional linkers. One functional group of this linker is reactive to the functional groups attached to termini of the polymer chains, preferably thiols. The other functional group of the linker is capable of nonspecifically tethering to the biomolecule of interest via its amine groups. The latter functional group is selected from the group consisting of succinimidyl active ester such as N-hydroxysuccinimide (NHS), succinimidyl alpha-methylbutanoate, succinimidyl propionate; aldehyde; thiol; thiol-selective group such as acrylate, maleimide or vinylsulfone; pyridylthioesters and pyridyldisulfide. Preferably NHS-PEG-maleimide linkers are attached to the biomolecules.

Site-selective tethering is needed for chimeric/tagged proteins having tags to enable binding to targets chosen from the group consisting of ProteinA, ProteinG, ProteinA/G, Streptavidin, NeutrAvidin, NTA, antibodies, S-fragment of RNaseA, calmodulin, cellulose, chitin, glutathione, amylose or functionalized oligopeptides and oligonucleotides having nucleophilic or electrophilic functional groups that can react with the functional groups on the hydrogel network.

The rigid substrate used serves as a support onto which the hydrogel is layered and is made of a typical cell culture substrate such as glass or plastic.

In preferred embodiments, the microarrays according to the invention possess a hydrogel layer thickness of between 50 μm to 1 mm, preferably of between 50 μm and 700 μm, most preferably of between 50 μm and 500 μm.

In preferred embodiments, there are 4 to 256 microwells on a hydrogel surface equivalent of 1 cm$^2$, preferably 4 to 64 microwells, more preferably 4 to 32, even more preferably 4 to about 8.

Preferably, each microwell has a diameter in the range of about 50 μm to about 1 mm, preferably of about 150 μm to about 800 μm, more preferably of about 200 μm to about 600 μm and even more preferably of about 300 μm to about 500 μm; the depth of a microwell preferably is in the range of about 10 μm to about 100 μm, preferably about 15 μm to about 70 μm, more preferably about 20 μm to about 50 μm and even more preferably about 30 μm to about 40 μm.

A further aspect of the invention is a method for preparing a topographically structured microarray comprising the steps a) to d), where a) is the robotic spotting or inkjet printing of one or more types of biomolecules on top of the micropillars of an array of micropillars, b) is the preparation of a partially crosslinked hydrogel attached to a rigid substrate, c) is the step of simultaneously soft-embossing a hydrogel microwell array while transferring and tethering biomolecules from the micropillars to the bottom of the microwells by pressing the micropillars of the array of step a) onto the partially crosslinked layer of hydrogel of step b) until the crosslinking is complete and step d) is the demolding of the array of micropillars of step a) from the hydrogel microwell array of step c).

In steps a) and c) of said method the biomolecules may e.g. be small molecules such as natural products or macromolecules selected from the group of proteins, oligopeptides or oligonucleotides, polynucleotides, oligo- or polysaccharides. The biomolecules employed are either known or expected to influence cell fate and fall into the categories of larger ECM proteins such as fibronectin, laminins, collagens and chimeric proteins having binding tags such as Fc-tagged N-Cadherin.

In step a) of said method for preparing a topographically structured microarray the array of micropillars may possess a topology matched to the spotting scheme of the robot such as a commercially available DNA spotter.

Alternatively, the topology of the array of micropillars of step a) can be chosen freely to match the printing scheme of an inkjet printer. Said printing scheme can be changed easily.

Further, the array of micropillars employed in step a) may be a silicon stamp with micropillars having diameters of 450 µm and heights of 80 to 100 µm.

Within step b) of the method for preparing a topographically structured microarray, the partially crosslinked hydrogel used is a soft, biomimetic, i.e. physiologically relevant, hydrogel.

This hydrogel is formed from a crosslinked hydrophilic polymer selected from the group consisting of poly(ethylene glycol), polyaliphatic polyurethanes, polyether polyurethanes, polyester polyurethanes, polyethylene copolymers, polyamides, polyvinyl alcohols, poly(ethylene oxide), polypropylene oxide, polyethylene glycol, polypropylene glycol, polytetramethylene oxide, polyvinyl pyrrolidone, polyacrylamide, poly(hydroxy ethyl acrylate), poly(hydroxyethyl methacrylate) or mixtures thereof; wherein the hydrophilic polymer has an excess of free functional groups, preferably nucleophilic groups, more preferably chosen from the group consisting of amines and thiols, and, in addition or alternatively, electrophilic groups, preferably chosen from the group consisting of acrylates, methacrylates, acylamides, methacrylamides, acylonitiriles, quinines, vinylsulfones, maleimides and their derivatives.

Preferably, a polyethylene glycol-based (PEG-based) hydrogel with an excess of free functional groups such as nucleophilic groups (e.g. thiols) and electrophilic groups (e.g. the conjugated unsaturated group vinylsulfone) is used. Preferably, an excess of 1.2 mM of free thiol groups within a PEG-based hydrogel is obtained.

The PEG-based hydrogel used in step b) of the method for preparing a topographically structured microarray is prepared by mixing and crosslinking of at least two precursor components using a chemical reaction, wherein the first precursor component comprises n nucleophilic groups and the second precursor component comprises m electrophilic groups, wherein n and m are at least two and the sum n+m is at least five, and wherein the crosslinking is preferably conducted between a multi-arm-PEG macromer, preferably a four-arm-PEG macromer having a molecular weight of 10 kDa and end-functionalized with nucleophilic, preferably thiol-groups, with a multi-arm-PEG macromer, preferably an eight-arm-PEG macromer having a molecular weight of 10 kDa and end-functionalized with electrophilic, preferably vinyl-sulfone-groups at appropriate concentrations and conditions such as to allow for the crosslinked hydrogel layer to exhibit a shear modulus between 1 and 100 kPa.

The resulting general dimension of the hydrogel (i.e. thickness, microwells per cm$^2$, diameter) as outlined hereinbefore apply mutatis mutandis to the method for preparing the hydrogel.

The rigid substrate of step b) of the method for preparing a microarray may be plastic or glass.

Optionally, step c) of the method for preparing a topographically structured microarray may be carried out using a press, which prevents movement of the array of micropillars in the xy-direction.

Further, said tethering of biomolecules within step c) of the method for preparing a topographically structured microarray occurs by attaching larger ECM proteins to the hydrogel by using linear, heterodifunctional NHS-PEG-maleimide linkers attached to the protein, which bind to free thiol groups of the hydrogel. If the biomolecules to be tethered are chimeric proteins having Fc-tags, ProteinA or ProteinG is covalently immobilized by the free thiol groups of the hydrogel followed by affinity-based binding of the chimeric protein to ProteinA or ProteinG.

The microwells soft-embossed into the hydrogel layer in step c) of the method for preparing a microarray have diameters of 450 µm and depths of 35±4 µm.

Employing a method according to the invention for preparing a topographically structured microarray, microarrays containing up to 2016 microwells on a surface of a standard glass slide of 18 cm2 can be obtained.

The method for preparing microarrays according to the invention takes approximately two hours and can be parallelized. Thus, up to ten large-scale arrays can be manufactured in less than 10 hours.

Another aspect of the present invention relates to an array of micropillars. Said array of micropillars, which can be made of silicon, serves as a stamp in the soft-embossing of a hydrogel in order to obtain a topographically structured microarray.

The dimensions and positions of its micropillars are matched to the spotting scheme of a spotting robot such as a commercially available DNA spotter. Said micropillars have heights of 80 to 100 µm and diameters of 450 µm and thus are equal to the diameters of the microwells, which they impress into the hydrogel of the microarray.

Alternatively, the topology of the array of micropillars of step a) can be chosen freely to match the printing scheme of an inkjet printer. Said printing scheme can be changed easily.

In one embodiment of the invention, an array of micropillars possesses 2016 micropillars arranged into seven fields of 12×24 micropillars each. Individual fields are separated from each other by 1750 µm. Each micropillar has a height of 80 to 100 µm and a diameter of 450 µm and the distance from the centre of one micropillar to that of another measures 750 µm.

Yet another aspect of the invention is a method for preparing an array of micropillars comprising the steps of
a) providing a photolithography mask preferably possessing the inverted pattern of the spotting scheme of a spotting robot such as a DNA spotter or the printing scheme of an inkjet printer, i.e. the positions and dimensions of the micropillars are matched to the spotting scheme of a spotting robot or the printing scheme of an inkjet printer,
b) covering a substrate such as a silicon wafer with a photoresist,
c) exposing the substrate to the photolithography mask of step a) for at least one exposure cycle with subsequent development of the photoresist and
d) etching the substrate to obtain the array of micropillars. Thereafter, the substrate is cleaned and any photoresist residues are removed by 30s oxygen plasma treatment.

A further aspect of the invention is a kit of parts comprising an array of micropillars according to the invention described above, a substantially planar and/or rigid substrate and the reactants necessary to form a hydrogel having a shear modulus of between 1 and 100 kPa in a substantially cured state. The elasticity of the hydrogel can be varied by tuning the shear modulus.

The rigid substrate, which is a part of the kit of parts, may be glass or plastic.

The reactants of the kit of parts, are reactants to form a PEG-based hydrogel having a shear modulus of between 1 and 100 kPa. More specifically, the reactants are 4arm-PEG macromers end-functionalized with thiol groups and possessing a molecular weight of 10 kDa and 8 am-PEG macromers end-functionalized with vinylsulfone groups and possessing a molecular weight of 10 kDa used in various concentrations to adjust stiffness of the hydrogel to be formed between 1 and 100 kPa and in such a way as to obtain an excess of 1.2 mM of free thiol groups. Further, a 0.3 M triethanolamine buffer having a pH of 8 is part of the kit of parts. In cases where the hydrogel is used for the immobilization of Fc-tagged proteins, PEG-comjugated ProteinA or ProteinG is also amongst the reactants comprised in the kit of parts.

EXAMPLES

Preparation of Thin Hydrogel Films

Thin layers of hydrogels were formed by crosslinking two poly(ethylene glycol) (PEG) macromers, end-functionalized the bulk of the gel (85 µg/ml). 350 µl of the prepared mix were transferred per chamber of a four-well plate (Nunc). A hydrophobic glass slide (treated with Sigmacote, Sigma-Aldrich) and coverslip-spacers were used to produce homogeneous and thin gel layers (ca. 170 µm).

ii) Preparation of Silicon Stamps

A photolithography mask was designed using CleWin (Phoenix), written as an inverted pattern on a five inch square chrome blank, and subsequently developed and etched in an etch bath. A four inch silicon wafer was primed using HDMS prior to spin-coating of a 10 µm thick layer of AZ9260 photoresist on an automated photoresist processing cluster (EVG150, EV Group). The wafer was exposed to the previously produced mask on a mask aligner for two cycles of 15s, followed by automated development of the photoresist. The silicon wafer was etched to a depth of 100 µm via DRIE (Alcatel601, AMMS). The topological features were confirmed on a surface profiler (Alpha-Step 500, Tencor). The produced wafer was then cleaned and photoresist residues were removed by a 30s oxygen plasma treatment.

iii) Preparation of Artificial Niche Microarrays

All the arrayed proteins, the concentrations used as well as the source are listed in Table I.

TABLE I

| # | Protein | Specie | Source | Immobilization | Concentration (mg/ml) | Molecular weight (kDa) |
|---|---|---|---|---|---|---|
| 1 | Laminin | *M. musculus* | BD biosciences | PEG linker | 1E+00 | 900 |
| 2 | Fibronectin frag. 9-10 | | Martino et al. 2009* | PEG linker | 8E-01 | 21 |
| 3 | N-Cadherin | *H. sapiens* | R&D | Fc/Prot. A | 1.5E-01 | 89.2 |
| 4 | Wnt-3a | *M. musculus* | R&D | PEG linker | 1.5E-01 | 37 |
| 5 | Jagged-1 | *R. rattus* | R&D | Fc/Prot. A | 2E-01 | 141.7 |
| 6 | Dkk-1 | *H. sapiens* | R&D | PEG linker | 1.5E-01 | 27 |
| 7 | BMP-8 | *H. sapiens* | R&D | PEG linker | 4E-01 | 15 |
| 8 | GDF-8 | *M. musculus* | R&D | PEG linker | 1.5E-01 | 12.4 |
| 9 | CCL2 | *H. sapiens* | R&D | PEG linker | 1.5E-01 | 8.7 |
| 10 | FGF-18 | *H. sapiens* | Peprotech | PEG linker | 4E-01 | 21.2 |
| 11 | Wnt-7a | *H. sapiens* | R&D | PEG linker | 4E-01 | 35.3 |
| 12 | VE-Cadherin | *H. sapiens* | R&D | Fc/Prot. A | 4E-01 | 92 |
| 13 | Shh | *H. sapiens* | R&D | PEG linker | 1.5E-01 | 20 |
| 14 | DR4 | *H. sapiens* | R&D | PEG linker | 1.5E-01 | 55.6 |
| 15 | TSH | *H. sapiens* | R&D | PEG linker | 4E-01 | 16-29 |
| 16 | Wnt-5a | *M. musculus* | R&D | PEG linker | 1.5E-01 | 33 |
| 17 | Dik1 | *H. sapiens* | Enzo life science | Fc/Prot. A | 1.5E-01 | 32 |
| 18 | BMP-2 | *H. sapiens* | R&D | PEG linker | 1.5E-01 | 15 |
| 19 | BDNF | *H. sapiens* | R&D | PEG linker | 5E-02 | 13.6 |
| 20 | CNTF | *H. sapiens* | R&D | PEG linker | 1E-01 | 22.8 |
| 21 | TGF-b | *H. sapiens* | Peprotech | PEG linker | 3.5E-03 | 25 |
| 22 | Jagged-1 | *H. sapiens* | R&D | Fc/Prot. A | 1.5E-01 | 137 |
| 23 | BSA | Bovine | Sigma | PEG linker | 1E+00 | 66 |

*M. M. Martino, M. Mochizuki, D. A. Rothenfluh et al, Biomaterials 30 (6), 1089 (2009)

with either thiol (SH) or vinylsulfone (VS) groups. 4arm-PEG-SH, mol. weight 10 kDa, and 8arm-PEG-VS (NOF Corporation), mol. weight 10 kDa, were mixed at various concentrations to adjust stiffness and stoichiometric ratio as reported. 5% (w/v) Gels with an excess of 1.2 mM SH groups were obtained by mixing 48.2 µl of PEG-VS (12% w/v) with 97.6 µl of PEG-SH (12% w/v). The final volume (350 µl) was reached by adding 204.2 µl of triethanolamine buffer (0.3 M, pH 8, Fluka). In cases where the hydrogel substrates were used for immobilization of Fc-tagged proteins, PEG-conjugated ProteinA (Biovision) was added to Protein candidates having no Fc-tag were modified with a heterobifuctional NHS-PEG-Maleimide linker (3.5 kDa, JenKem Technology). Printing solutions were composed of protein at the indicated concentration in PBS or Borate (0.1 M, pH8, Sigma-Aldrich) containing 30% (v/v) glycerol. A 384-microtiter plate (Genetix Ltd.) was filled with 5 to 10 µl of printing solution per well. The relative positions of the protein solutions in the wells were arranged to meet the experimental designs (homogeneous arrays, overlapping gradients or randomized design). Silicon stamps and microtiter plate were loaded into a Qarray mini robotic spotter (Genetix Ltd.) (FIG. 1a, (1) to (3)). Spotted silicon stamps were then pressed onto the partially crosslinked hydrogel substrate for two hours (FIG. 1a, (4) to (5)). Arrays were de-molded (FIG. 1a, (6)) and extensively washed with PBS followed by a UV sterilization. Artificial niche microarrays used for adherent cell culture (MSCs) were treated overnight in a 0.1% (w/v) Pluronic F127 solution (Sigma-Aldrich) to minimize nonspecific cell attachment outside of microwells.

Figure 2A:
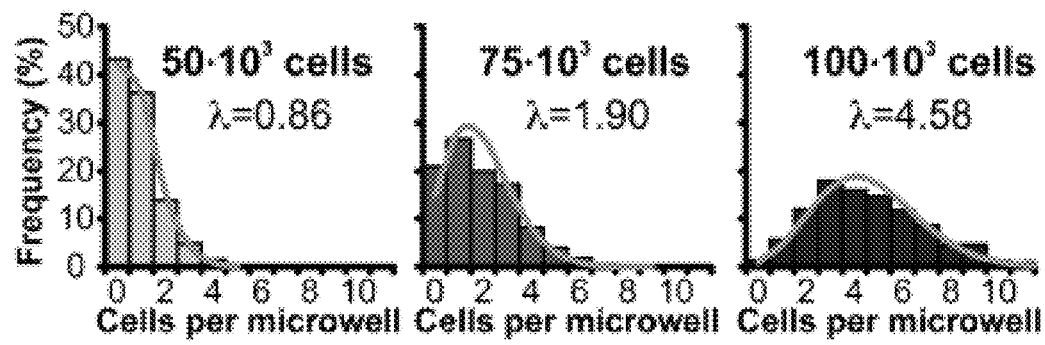
FIGS. 2 a to e show the modulation of mesenchymal stem cell (MSC) seeding concentration and its effect on adipogenic differentiation, cell shape and proliferation: (a) 5.103, 7.5.103 and 10.103 MSC are seeded on each array. The distribution of cells per microwell at day 0 follows a Poisson law (grey line) where y is determined by the amount of seeded cells. (b) Quantification of proliferation, differentiation and cell shape. Phase contrast microscopy is performed at day 0 to count the number of cells in each microwell. After 11 days of culture in adipogenic medium, cells are fixed and stained with Nile Red and Phalloidin-Alexa488 to quantify indexes of differentiation, proliferation and cell shape, respectively. (c, d, e) Increasing the initial cell density results in increased adipogenic differentiation and reduced dispersion from the mean (horizontal bars). Cell size and proliferation followed an opposite trend. Scale bars equal 100 µm. Error bars represent the Standard Error of the Mean (SEM).
Figure 2B:
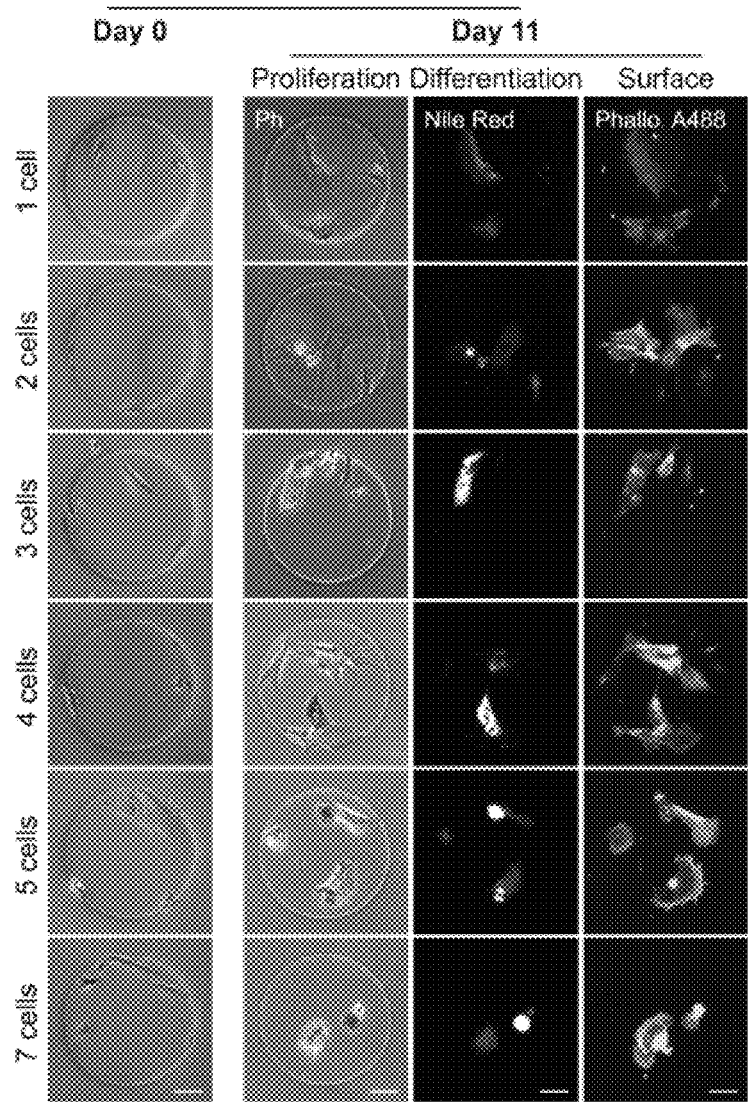

Immunostaining was performed to verify the quality of the protein transfer to the microwells. FN9-10 spotting was assessed by first fixing the arrays with PFA (4%, 15 min) followed by incubation with anti-fibronectin (1:100) monoclonal mouse antibody (Chemicon-Millipore, Billerica, Mass., USA). N-Cadherin spotting was assessed using an anti-N-Cadherin (1:100) monoclonal mouse antibody (R&D systems, Minneapolis, Minn., USA). If protein A was present in the gel, free Fc-binding sites were passivated with a solution of human IgG (Sigma-Aldrich) at 1 mg/ml in order to improve contrast. Primary antibodies were stained by anti-mouse (1:400) Alexa Fluor secondary antibodies (Life Technologies-Invitrogen, Carlsbad, Calif., USA).

iv) Probing the Effect of Cell Density on Adipogenic Differentiation of Adherent MSC Three different concentrations of primary human mesenchymal stem cells (MSCs) were seeded onto artificial niche microarrays, resulting in distinct Poisson distributions of cells per microwell (FIG. 2a). To facilitate selective cell adhesion and spreading of MSCs, microwells were homogeneously functionalized with cell-adhesive fibronectin fragment 9-10 (FN9-10). MSCs were stimulated to differentiate into adipocytes by culturing them in medium supplemented with dexamethasone, 3-Isobutyl-1-methylxanthine and indomethacin. After 11 days in culture, the extent of proliferation and differentiation, as well as the cell shape were determined by staining nuclei (by Dapi), lipid vesicles (Nile red) and actin filaments (Phalloidin), respectively (FIG. 2b). The measured parameters were quantified as indexes (averaged per cell) for each microwell (FIG. 2c-e). The presence of increasing numbers of cells per microwell at the onset of the experiment resulted in increased adipogenic differentiation (FIG. 2c). This effect is particularly clear when coefficients of variation (CV) are compared. In the population of one cell per microwell at day 0, a CV of 214% was measured, in contrast to the population of twelve cells at day 0, which resulted in a CV-decrease by a factor of three (66%). Notably, the exact opposite behaviors were observed for proliferation (FIG. 2d) and cell surface indexes (FIG. 2e), where increasing adipogenic differentiation was accompanied by lower average cell surface areas and, as expected, less proliferation.

v) Mimicking Cell-cell Interactions by Localized N-Cadherin Display

Figure 3A:
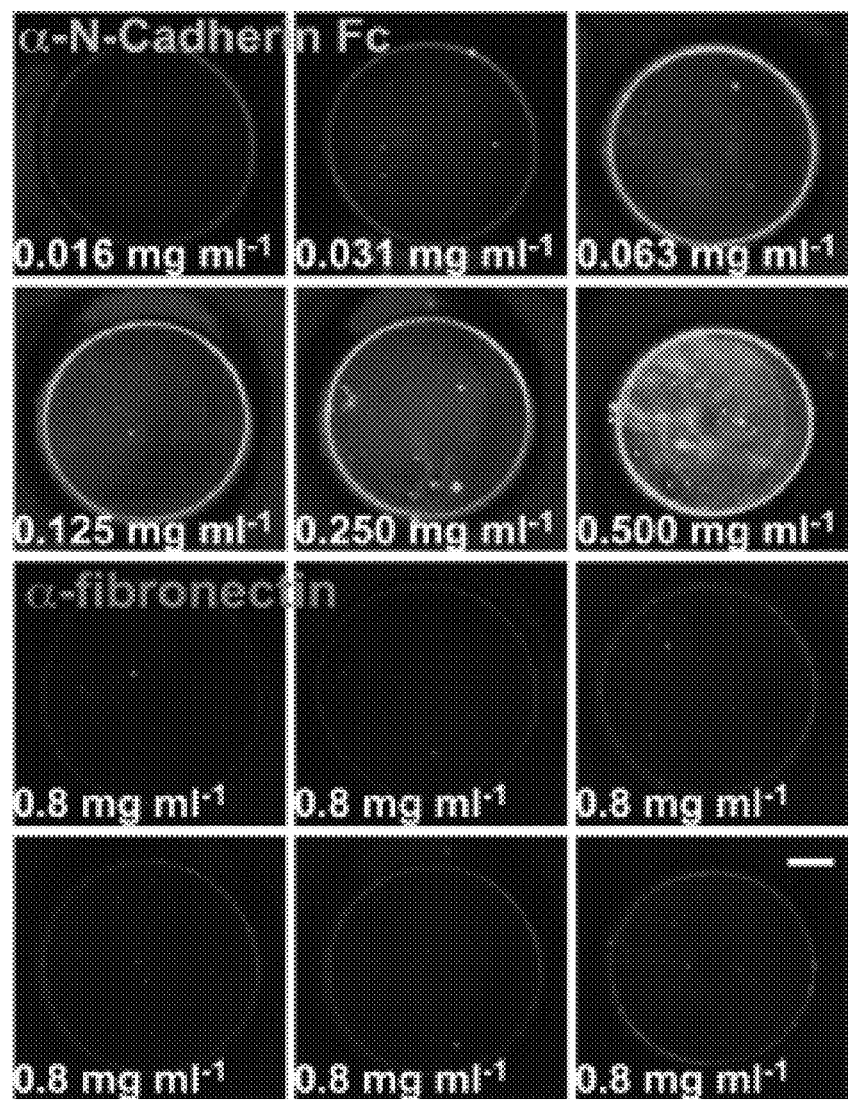
FIGS. 3 a to h depict the biochemical recapitulation of the cell density effect of adipogenic differentiation of mesenchymal stem cells (MSCs), where (a, b) show the localized functionalization of microwell arrays with variable concentrations of N-Cadherin on a constant background level of FN9-10. Immunostaining with anti-N-Cadherin and quantification by fluorescence microscopy demonstrate the well-controlled co-functionalization with these two biomolecules in the same microwells. (c) shows the phase contrast, Phalloidine-Alexa488 and Nile Red images of MSCs exposed to various concentrations of N-Cadherin (11 days). (d) shows the increasing concentrations of N-Cadherin resulting in an average increase of adipogenic differentiation across all cell densities. (e) shows N-Cadherin decreasing the cell surface index. (f) shows tethered N-Cadherin influencing adipogenic differention in a dose-dependent manner, when only the microwells with one, three or five initial cells are considered. (g) shows that within microwells displaying high concentration of N-Cadherin (0.250 mg/ml) significantly ($p<0.001$) higher levels differentiation compared to the control (0.016 mg/ml) are reached already with a single cell at the onset of the experiment. Intermediate N-Cadherin concentrations need four cells to reach significantly ($p<0.05$) higher differentiation levels. The horizontal dashed line represents the average adipogenic differentiation across all microwells. (h) shows that when N-Cadherin is blocked, adipogenic differention decreases in a manner dependent on the initial cell density per microwell. (i) shows that the decrease in adipogenic differentiation is also a function of the N-Cadherin concentration. (N.I.A.D.=Normalized Index of Adipogenic Proliferation; A.U.=Arbitrary Unit.) Error bars represent SEM. Scale bars equal 100 µm. *,  and * significant at $p<0.001$, $p<0.01$ and $p<0.05$, respectively.
Figure 3B:
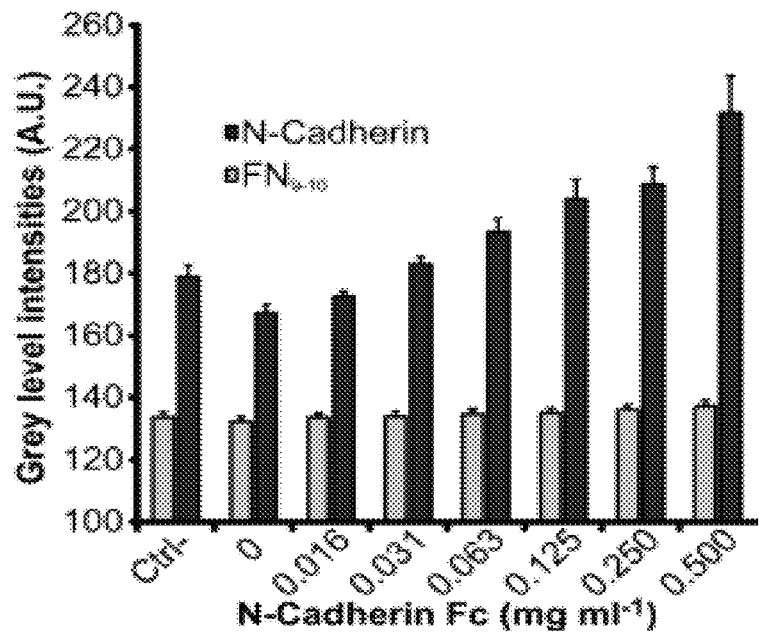
Figure 3C:
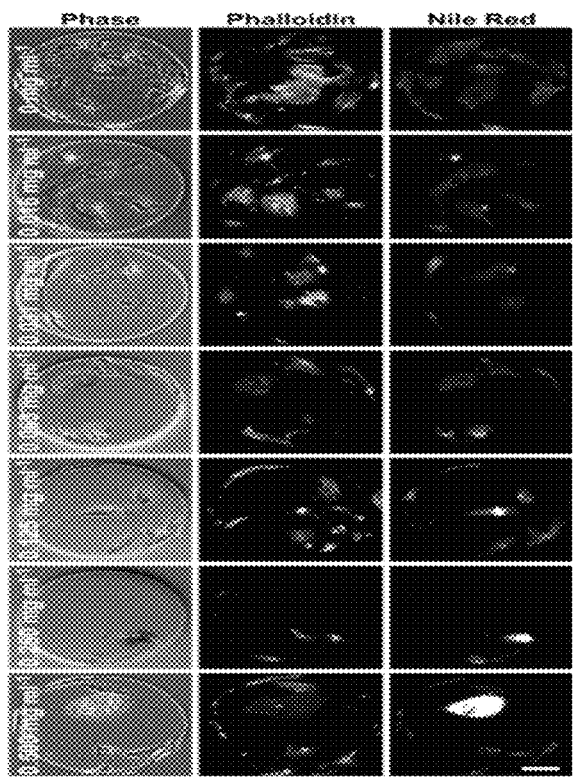

To test whether it was possible to biochemically mimic cell-cell interactions in artificial niches, microwell arrays were co-functionalized with amounts of 0, 0.016, 0.063 and 0.5 mg/ml of recombinant N-Cadherin-Fc (using the ProteinA affinity binding strategy), keeping constant in each microwell the concentration of FN9-10 at 0.8 mg/ml required for cell adhesion (FIGS. 3a and 3b). N-Cadherin significantly increased adipogenic differentiation in a concentration-dependent manner across all microwells (FIGS. 3c and 3d). Concomitantly, increasing concentrations of N-Cadherin decreased the average cell surface area (FIG. 3e) and decreased proliferation. The effect on differentiation seemed to be independent of the initial cell density (FIG. 3f). However, a reduction in cell attachment at highest N-Cadherin concentration (0.5 mg/ml) was noticed. The latter could either be caused by a biological mechanism such as a crosstalk between integrin and homotypic or heterotypic Cadherin in teraction, or simply due to the presence of high amounts of N-Cadherin masking the binding of integrins to FN9-10. To test the latter possibility, the attachment of MSCs on various FN9-10 concentrations was investigated and no significant differences ($p<0.05$) across a wide concentration range (0.063 to 1.6 mg/ml of FN9-10) was found. This suggested that direct masking is unlikely. Despite reduced cell attachment, cells on the two highest N-Cadherin concentrations tested (0.25 and 0.5 mg/ml), showed increased differentiation compared to the controls ($p<0.001$ and $p<0.01$, respectively). In microwells with for example one, three or five cells at day 0, the average increase of differentiation correlated with the N-Cadherin concentration matching a power law (FIG. 3f). It was observed that for reaching significantly higher levels of differentiation compared to the control (0.016 mg/ml N-Cadherin), only one cell for 0.250 mg/ml and four cells for 0.063 mg/ml were needed (FIG. 3g).

To prove the specificity of the observed N-Cadherin effect on adipogenic differentiation, a function-blocking antibody directed against the extracellular domain of N-Cadherin, anti-N-Cadherin mouse monoclonal antibody (Clone GC4, Sigma-Aldrich, Germany), was used. Two microarrays were pre-incubated for 30 min at 37° C. with 12 µg/ml anti-N-Cadherin mouse monoclonal antibody solution before cell seeding. As a control, two arrays were incubated with purified human IgG (Sigma-Aldrich, Germany) at the same concentration. Both antibodies were maintained at the same concentration in adipogenic medium during the entire cell culture period of 11 days. Finally, adipogenic differentiation was quantified in every microwell as described above.

This experiment showed that blocking N-Cadherin on the microwell arrays efficiently reduced adipogenesis across all initial cell numbers per microwell (FIG. 3h). It was also observed that the extent of inhibition was a function of the amount of tethered N-Cadherin (FIG. 3i); the highest N-Cadherin concentration showed the strongest inhibition of adipogenic differentiation. Together, these data highlight the importance of controlling the cell-seeding concentration, a parameter that is often overlooked in probing stem cell fate in vitro. Moreover, it is also demonstrated that cell-cell interactions can, for example, be mimicked on our artificial niche microarray platform by local biochemical functionalization of microwells with Cadherins.

vi) Probing the Effect of Stiffness on Osteogenic Differentiation of MSC

Figure 4A:
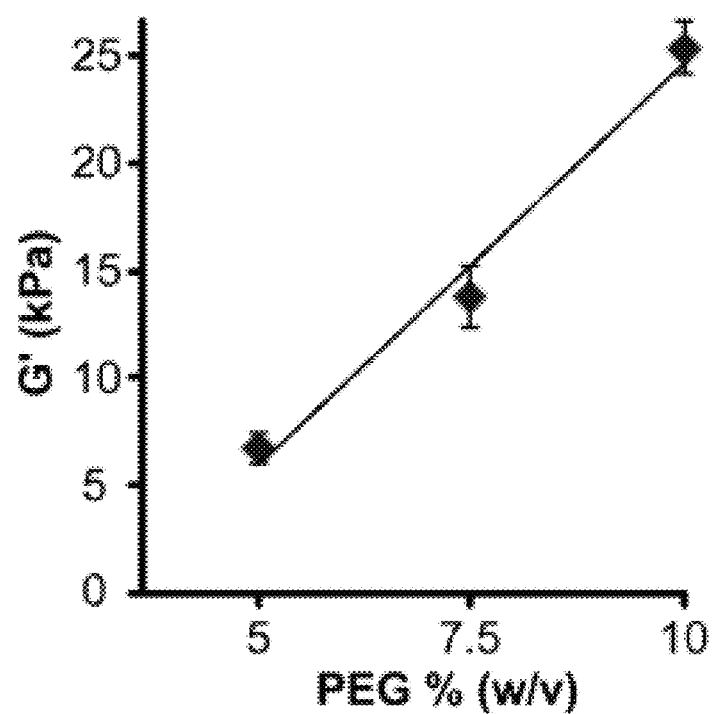
FIGS. 4 a to f depict the effect of matrix stiffness on osteogenic differentiation of MSCs. (a) The shear moduli G' of the substrates are varied by tuning PEG precursor concentrations (w/v). Obtained values range between ca. 6-26 kPa, corresponding to E-moduli of between ca. 20-75 kPa (assuming a Poisson ration of 0.5) (b) Immunostaining of immobilized fibronectin show that stiffness modulation of the array does not influence the extent of protein immobilization. (c) Alkaline phosphatase and Dapi stains of MSCs cultured for 11 days on various stiffnesses in osteogenic medium. (d,e) An increase in stiffness significantly increases osteogenic differention and cell shape. (f) The stiffness effect is independent of the FN9-10 concentration. Scale bars equal 100 µm. *,  and * significant at $p<0.001$, $p<0.01$ and $p<0.05$, respectively.
Figure 4B:
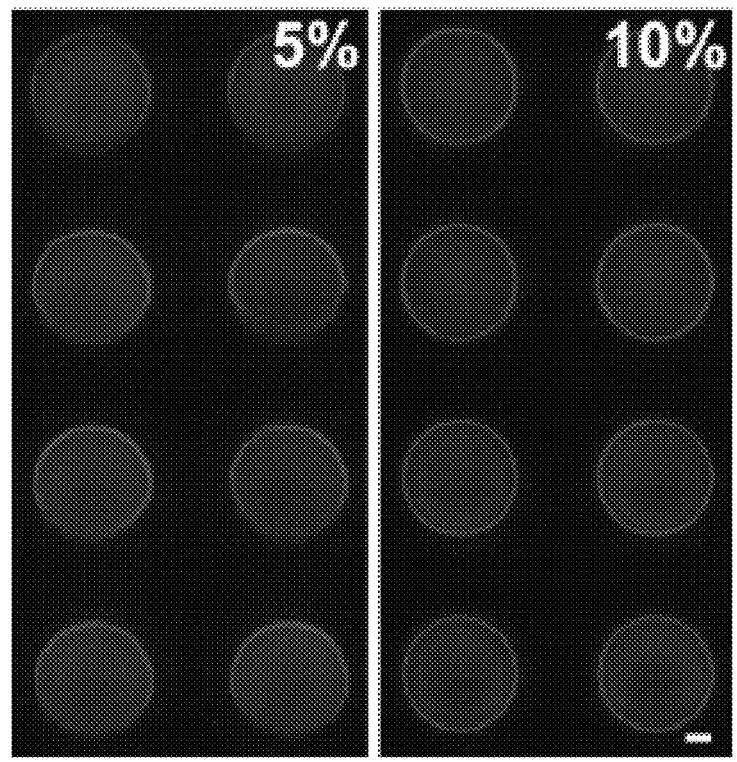

Hydrogel films at three different PEG precursor concentrations (5, 7.5 and 10%), resulting in a linear increase in gel crosslinking density and shear moduli between 6-26 kPa (FIG. 4a), were formed. Importantly, the molarity of free functional groups necessary for biomolecule tethering was kept constant (1.2 mM) across the three gel types, in order to be able to decouple the elastic moduli variation from the biochemical functionalization. Indeed, as determined by immunofluorescence, comparable amounts of FN9-10 were attached to gels having different elastic moduli (FIG. 4b). Furthermore, to elucidate whether substrate elasticity and cell adhesivity, induced by integrin-binding to FN9-10, might influence osteogenic differentiation of MSCs in a cooperative fashion, arrays of variable stiffness at eight different FN9-10 concentrations were prepared.

Figure 4C:
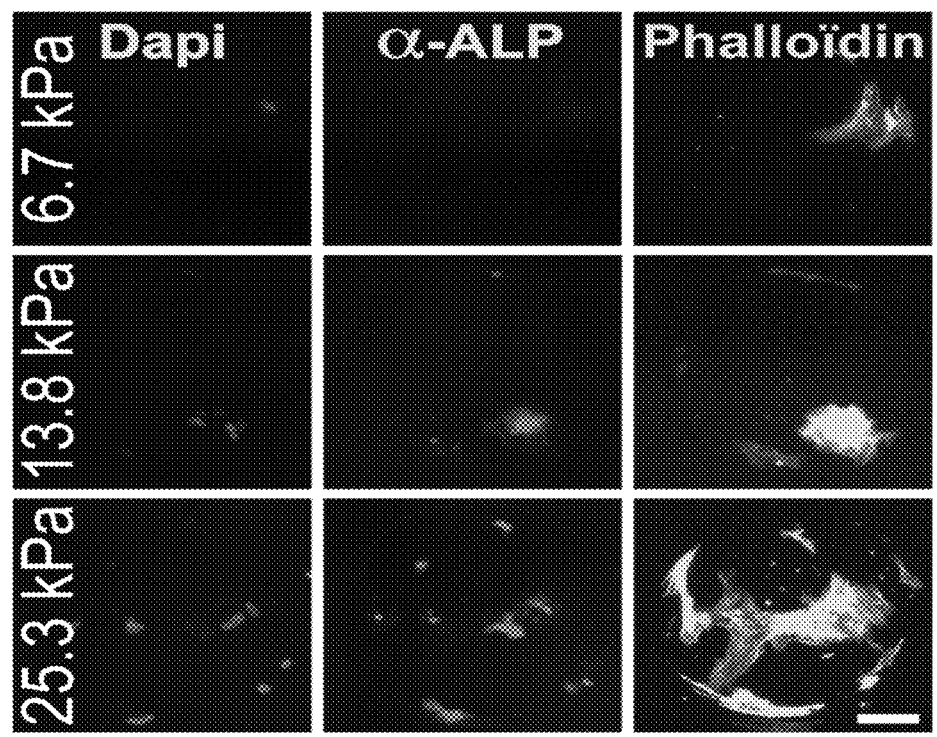

Increasing the elastic modulus of the substrate resulted in increased osteogenic differentiation of MSCs (FIGS. 4c and 4d), an effect that might be linked to changes in cell shape (FIG. 4e). Notably, this effect was independent of the FN9-10 concentration (FIG. 4f). Therefore, the microarrays according to the invention can not only be utilized to probe the influence of biophysical cues on cell fate, but also to parse biophysical and biochemical microenvironmental cues controlling a particular stem cell fate.

vii) Screening of Signaling Microenvironments to Deconstruct the Neural Stem Cell Niche.

Figure 5A:
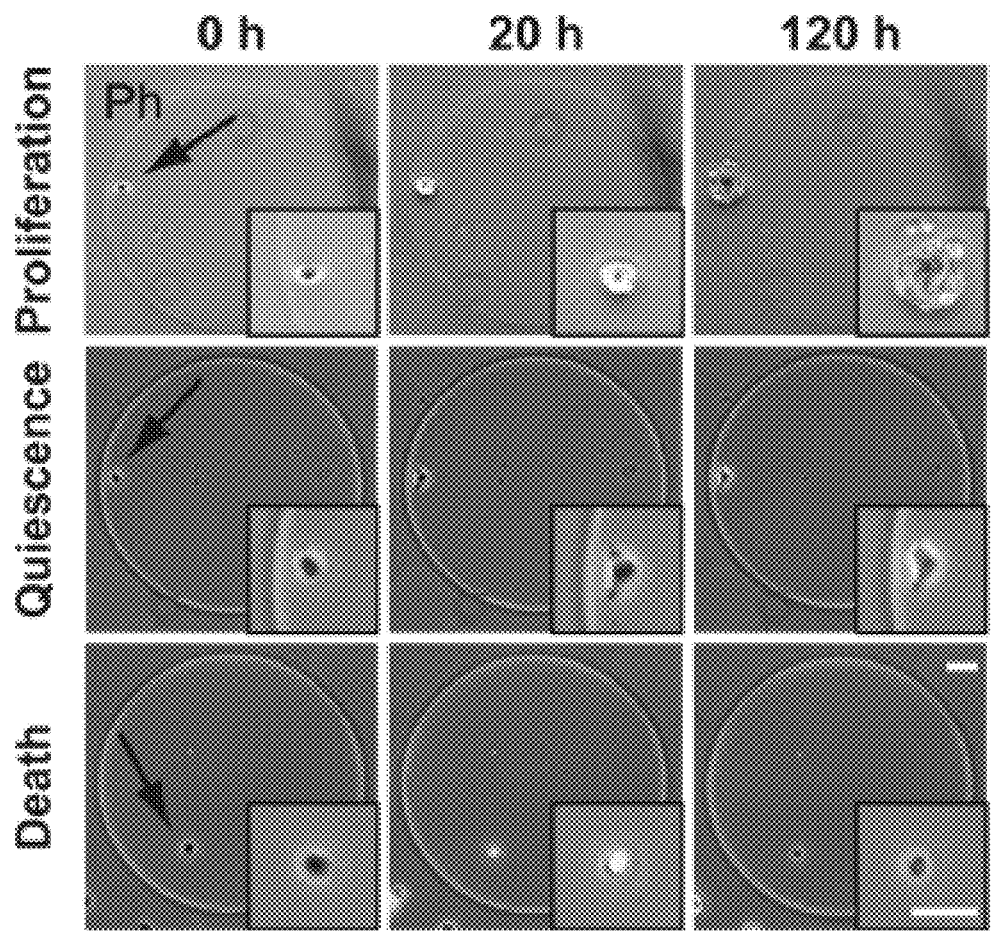
FIGS. 5 a to c depict the screening for the effects of 21 proteins on stem cell fate.
(a) shows selected frames of a time-lapse experiment showing proliferation, quiescence or death of single cells confined to microwells. Arrowheads indicate the initial single cell. Zooms on the single cells or neurospheres are shown in inserts. (b) depicts that arrays printed with only Jagged or Laminin show a dose-dependent increase of proliferation. Intermediate concentrations of Laminin induce slower proliferation. (c) shows that no additive effect of Laminin and Jagged1 is observed. *, , * significant at $p<0.001$, $p<0.01$ and $p<0.05$, respectively in a $\chi 2$ test. Error bars represent SEM. Scale bar equal 100 µm.

An array of putative protein candidates involved in regulating self-renewal of single murine non-adherent neural stem cells (NSCs) (FIG. 5) was screened. Sphere-forming NSCs were isolated from subventricular regions of postnatal Hes5-GFP transgenic reporter mice and cultured in the presence of epidermal growth factor (EGF). In this system, the expression of GFP under the control of the promoter of Hes5, a transcription factor downstream of activated Notch signaling, marks multipotent stem and progenitor cells of the developing and postnatal/adult brain. The multilineage differentiation potential of these cells was confirmed both on standard plastic culture dishes and on the microwell array. Cells expressing markers of the three neural lineages (neurons, astrocytes and oligodendrocytes) were obtained from neurosphere-forming NSCs. 21 candidate NSC regulatory proteins were chosen and immobilized at the bottom of microwells. Each protein was present in 72 microwells per microarrays. To maximize the percentage of microwells bearing just one cell, only $10^4$ NSC were seeded per array. Time-lapse microscopy was performed on live cells to monitor the entire array in a mosaic-like fashion over five days and with a time interval of three hours. The microwell topography allowed reliable long-term trapping of NSCs. For each single cell trapped in a microwell it was quantified whether or not it proliferated (absence of proliferation termed 'quiescence' here), or whether it died during the time observed (FIG. 5a). In addition, neurosphere sizes were measured by semi-automated image analysis.

In the presence of soluble EGF as medium supplement, approximately 67% of all single NSC in plain PEG microwells proliferated extensively, producing neurospheres of variable sizes. Immunostaining of clonally derived neurospheres revealed the presence of the stem/progenitor cell markers Nestin, GFAP and HES5, as well as the absence of the neuronal differentiation marker βIII-tubulin. The protein candidates showed contrasting effects on single NSC fate. For example, the Notch ligands Jagged1 and DLL4 were found to induce the most extensive proliferation. Laminin1 and CNTF were also found to have a positive effect on NSC proliferation. In contrast, cells in microwells with tethered Wnt3a and Wnt5a showed less proliferation compared to the control. When neurosphere sizes at day 5 were quantified, the Notch ligands were found to induce significantly larger sphere sizes compared to the blank control (p<0.001). Interestingly, some proteins had apparently discrepant behaviours, inducing less cells to proliferate but those that did; formed larger neurospheres (e.g. Wnt5a), or vice versa (e.g. BMP6). These effects could hint to unpredicted modes of action or a signaling influence on a particular sub-population of cells.

Figure 5B:
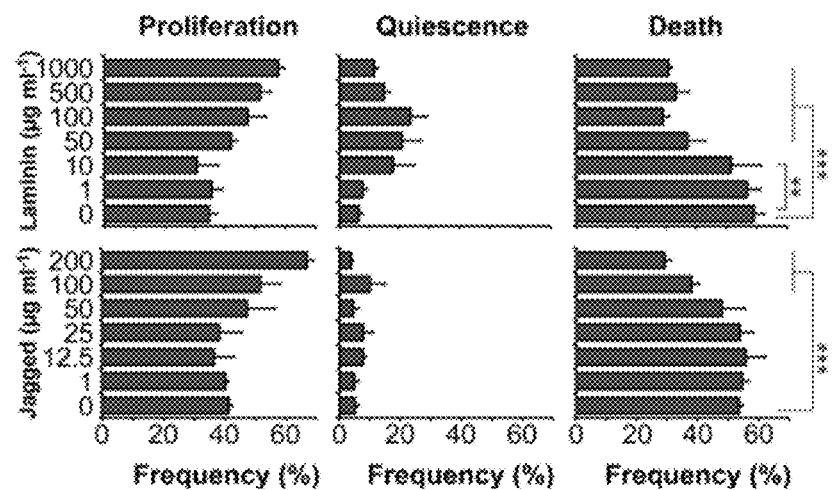
Figure 5C:
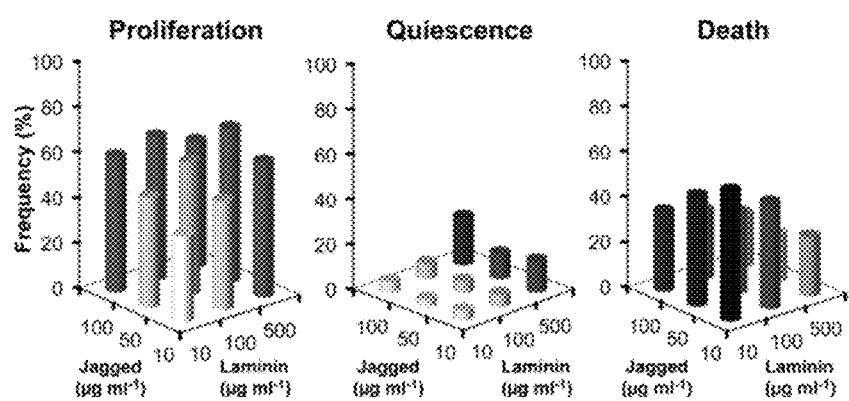

To further investigate the effects of the basal lamina protein component Laminin1 and the Notch ligand Jagged1, two previously identified components of the native NSC niche, microwell arrays in which these proteins were spotted at various concentrations, singly or in combination, were prepared. Presented alone, both proteins were found to positively influence NSC proliferation in a dose-dependent manner (FIG. 5b). However, we noticed that intermediate concentrations of Laminin1 clearly favoured quiescence, whereas Jagged1 did not alter the basal quiescence level. Moreover, when combinations of Laminin1 and Jagged1 were spotted at nine different ratios, no significant additive effect was observed (FIG. 5c), suggesting that the presence of either protein sufficed for reaching maximal proliferation under the chosen culture conditions containing high concentrations of EGF. In this combinatorial protein experiment, increased quiescence was again observed in the Laminin1-functionalized microwells, independent on the presence of Jagged1, suggesting a dominant effect of Laminin1 on quiescence.

These data highlight the usefulness of the presented platform for the fate analysis of single, non-adherent stem cells in response to more complex artificial niches. The combination of single cell trapping by topography with combinatorial tethering of protein candidates enables probing cell behavior in a manner previously not possible.

viii) Cell Culture

Human MSCs were generously provided by Maximilian Emmert and Simon Hoerstrupp (University Hospital Zurich). These cells were extracted from the bone marrow of two healthy human donors. Flow cytometry was performed on P1 cells to confirm the presence of the surface markers CD13, CD90, CD73, CD29, CD166, CD105 and the absence of the markers CD45, CD31 and CD34. Cells were expanded to passage 3 in proliferation medium containing α-MEM (Invitrogen), 10% FBS (Hyclone), 1 ng/ml FGF2 (R&D Systems), 2 mM L-glutamine (Sigma-Aldrich), penicillin and streptomycin (Invitrogen). Adipogenic potential was verified by culturing MSC in adipogenic medium consisting of low glucose DMEM (Invitrogen), 20% FCS (Hyclone), 0.5 mM IBMX (Sigma-Aldrich), 60 μM indomethacin (Fluka) and 1 μM dexmethasone (Sigma-Aldrich). Osteogenic potential was assessed by culturing MSC in osteogenic medium consisting of high glucose DMEM (Invitrogen), 10% FCS (Hyclone), 10 mM β-glycerophosphate (Sigma-Aldrich), 0.1 μM dexmethasone (Sigma-Aldrich) and 50 μg/mL L-ascorbic acid (Sigma-Aldrich). For seeding on the arrays, p3 cells were unfrozen and seeded in T75 flasks and cultured for 24 hours in proliferation medium. Trypsinized cells were counted and their concentration was adjusted (50E3, 75E3, 100E3 for adipogenic arrays and 40E3 cells for osteogenic arrays, respectively). In parallel, freshly prepared arrays were pre-incubated in proliferation medium not containing FGF2. Cells were seeded in 4 ml of medium and left to adhere for one hour. Cells that did not sediment in the microwells or that did not adhere were washed off with PBS. Adipogenic or osteogenic differentiation was induced by culturing cells in the appropriate media for 11 days or 14 days, respectively.

Epidermal growth factor (EGF)-dependent neurosphere cultures were generated from subventricular regions of postnatal (p5) Hes5-GFP transgenic mice or WT siblings. Briefly, subventricular regions were dissociated in 300 μL of a 1:1 papain: ovomucoid mix, at 37° C. for 45 min. The cell suspension was centrifuged (5 min at 80 g), dissociated, re-suspended and cultured in suspension in neurosphere medium (DMEM/F12+Glutamax, Invitrogen) containing 20 ng/mL EGF (R&D), and 1×B27 supplement (Invitrogen) for 4 days at 37° C. Obtained neurospheres were passaged with 0.05% trypsin in Versene (Invitrogen) followed by mild mechanical trituration, and expanded. Neurospheres were frozen at passage 2. Arrays were seeded with 10E3 dissociated cells (p3-p6).

ix) Cell Fate Determination

MSCs cultured on microarrays were fixed at day 11 (adipogenic differentiation) or at day 14 (osteogenic differentiation) in 4% paraformaldehyde (Fluka) for 15 minutes at room temperature. Permeabilization was used only when immunostainings were performed (osteogenic differentiation). Adipogenic differentiation was detected by staining the lipid vesicles with a solution (1 μg/ml in PBS) of Nile red (Sigma-Aldrich). Cell shape was determined by staining with phalloidin-Alexa488 (Invitrogen) following the manufacturer's instructions. A mouse anti-alkaline phosphatase antibody (R&D systems) was used (1:100) to assess osteogenic differentiation. In all cases DAPI (Sigma-Aldrich, 10 μg/mL) was used to stain nuclei.

Neurosphere-forming NSCs on the arrays were fixed in 4% paraformaldehyde in PBS for 15 minutes at room temperature, permeabilized with 0.1% TX-100 for 5 minutes and incubated for two hours in blocking buffer (PBS containing 0.01% TX100 in presence of 2% BSA and 0.5 mg/ml human IgG to saturate the remaining active sites of protein A). The primary antibodies mouse anti Laminin1 (Sigma), mouse anti-nestin (BD Transduction Laboratories), rabbit polyclonal anti GFP (Abcam), rabbit anti-βIII-Tubulin (Abcam) and mouse anti-βIII-Tubulin (R&D systems) were incubated in blocking solution for two hours at room temperature (1:100). Arrays were then washed in PBS and incubated for one hour at room temperature with Alexa-fluor-conjugated secondary antibodies (Invitrogen, 1:400) and DAPI (Sigma, 10 μg/mL). To probe the differentiation potential of putative NSCs, neurospheres were collected after five days of culture and directly plated on poly(L-lysine)-coated (0.001%) dishes. Differentiation was induced by reducing EGF concentration to 0.2 ng/ml or in medium supplemented with 1% FBS and 1ØM retinoic acid in neurobasal medium. After 10 days, cells were fixed in 4% paraformaldehyde for 15 min. Permeabilization and blocking was carried out in solution containing 0.1% TX-100 and 2% BSA. Immunostaining was performed as described above using rabbit anti-GFAP (Abcam) to mark astrocytes, rabbit anti-βIII-Tubulin (Abcam) to mark neurons, and mouse anti-O4 (R&D systems) to mark oligodendrocytes.

x) Microscopy and Image Analyses

Artificial niche microarrays seeded with MSCs were imaged at day 0 (phase contrast) and day 11 (phase contrast and fluorescence) using an inverted microscope (Zeiss Axio Observer Z1) equipped with a motorized Zeiss scanning stage and an incubator for live-cell imaging. Metamorph software (Molecular Devices) was used to control the xyz-stage. A script based on the "scan slide" function was used to acquire and stitch images corresponding to a field of view comprising 12×24 microwells. At day 0, the number of cells in each microwell was counted manually. At day 11 or 14, the number of cells per microwell was assessed automatically based on the DAPI images and by the "count nuclei" program of Metamorph. Proliferation index was defined as the ratio of cell number in every well at D0 and D11 or D14. To determine differentiation indexes in every microwell, Nile red fluorescent images were manually thresholded. Alkaline phosphatase signal acquisition was based on a local threshold around each nucleus. 98.2% of the median value measured under the nucleus area was considered as a positive alkaline phosphatase stain. The intensity of the fluorescent signal in every microwell was integrated over its surface. The obtained value was then normalized to the number of cells counted in DAPI (day 11). When indicated, the index of differentiation was normalized to the number of cells counted at day 0 or to the overall intensity of the entire array to allow comparisons between arrays. The cell shape index was obtained by applying an identical manual threshold method on phalloidine-alexa488-stained images. Comparable normalizations to the one mentioned above were applied (normalization to the number of cells or to the array).

xi) Quantitative PCR

Cultured human MSCs were trypsinized and RNA isolated using the RNeasy Plus Micro Kit (Qiagen, Valencia, Calif., USA). RNA quality was confirmed on a Bioanalyzer chip (Agilent Technologies, USA). Total RNA was reverse transcribed in a final volume of 20 μL using the iScript cDNA synthesis kit (Biorad, Hercules, Calif., USA). After reverse transcription, cDNA corresponding to 2 ng of initial RNA was used for one-step real-time quantitative PCR carried out with SYBR Green Supermix (Biorad, Hercules, Calif., USA) on an ABI Prism 7900HT Sequence Detection System (Applied Biosystems, Foster City, Calif.). The PCR program consisted of an initial UDG incubation step at 50° C. for 2 min, a template denaturation/enzyme activation step at 95° C. for 10 min, followed by 40 cycles at 95° C. for 15 sec with annealing and extension at 58° C. for 1 min. Primers used in real-time PCR were as follows: N-Cadherin forward 5'-GGCAGAAGAGAGACTGGGTC-3' and reverse 5'-GAGGCTGGTCAGCTCCTGGC-3'; LPL forward 5'-GAGATTTCTCTGTATGGCACC-3' and reverse 5'-CTGCAAATGAGACACTTTCTC-3'; GAPDH forward 5'-GAAGGTGAAGGTCGGAGTC-3' and reverse 5'-GAAGATGGTGATGGGATTTC-3'. Each sample was measured in a final volume of 10 μL and in triplicates. The amount of each amplification product was determined relative to the housekeeping gene GAPDH. Normalized values of adipogenic differentiation were compared to the proliferation control condition.

xii) Statistical Analysis

Standard two tailed T and $\chi^2$ tests were performed in R V2.11. When multiple comparisons were performed, p-values were adjusted using the p.adjust procedure with the "Bonferroni" option. The GLM procedure of SAS v9.0 software (SAS Institute) was used to test the significance of neurosphere size variation as a function of the spotted proteins, the arrays and the repeats. Differences of LSmeans±standard errors with the control were tested for significance. The same procedure was used to explain the variability of adipogenic differentiations and cell shape. The used models considered the effects of array, randomization, number of cells at day 0 and N-Cadherin or FN9-10 concentration. For all parametric tests, normality of the residues and homogeneity of the variance were examined in QQ and Tukey-Anscombe plots respectively. Log and square root transformations were utilized when it improved the normality of the residues.

The invention claimed is:

1. A method for preparing a topographically structured microarray, comprising the steps of
    a) providing one or more types of biomolecule(s) on top of micropillars of an array of micropillars;
    b) providing a partially crosslinked hydrogel on a substrate;
    c) simultaneously soft-embossing a hydrogel microwell array and transferring the biomolecule(s) from the micropillars to the microwells by pressing the micropillars of the array of step a) onto the partially crosslinked layer of hydrogel of step b) until substantial completion of crosslinking occurs; and
    d) demolding the array of micropillars of step a) from the hydrogel microwell array of step c).

2. The method according to claim 1, wherein the topology of the array of micropillars of step a) is matched to a spotting scheme of a spotting robot.

3. The method according to claim 1, wherein the topology of the array of micropillars is chosen freely to match a dispensing scheme of a liquid dispenser.

4. The method according to claim 3, wherein the liquid dispenser is an inkjet printer.

5. The method according to claim 1, wherein the biomolecules of step a) are natural products or macromolecules selected from the group of proteins, oligopeptides or oligonucleotides, polynucleotides, oligo- or polysaccharides.

6. The method according to claim 1, wherein the hydrogel is composed of or comprises a hydrophilic polymer selected from the group consisting of poly(ethylene glycol), polyaliphatic polyurethanes, polyether polyurethanes, polyester polyurethanes, polyethylene copolymers, polyamides, polyvinyl alcohols, poly(ethylene oxide), polypropylene oxide, polyethylene glycol, polypropylene glycol, polytetramethylene oxide, polyvinyl pyrrolidone, polyacrylamide, poly(hydroxy ethyl acrylate), poly(hydroxyethyl methacrylate), or mixtures thereof;

wherein the hydrophilic polymer has an excess of free functional groups.

* * * * *